US009696204B2

(12) United States Patent
Liu et al.

(10) Patent No.: US 9,696,204 B2
(45) Date of Patent: Jul. 4, 2017

(54) DETERMINATION AND CORRECTION OF FREQUENCY REGISTRATION DEVIATIONS FOR QUANTITATIVE SPECTROSCOPY

(71) Applicant: SpectraSensors, Inc., Rancho Cucamonga, CA (US)

(72) Inventors: Xiang Liu, Rancho Cucamonga, CA (US); Gary Yeh, Rancho Cucamonga, CA (US); Adam S. Chaimowitz, Rancho Cucamonga, CA (US); William Jenko, Rancho Cucamonga, CA (US); Alfred Feitisch, Los Gatos, CA (US)

(73) Assignee: SPECTRASENSORS, INC., Rancho Cucamonga, CA (US)

( * ) Notice: Subject to any disclaimer, the term of this patent is extended or adjusted under 35 U.S.C. 154(b) by 29 days.

(21) Appl. No.: 14/817,119

(22) Filed: Aug. 3, 2015

(65) Prior Publication Data

US 2017/0038257 A1 Feb. 9, 2017

(51) Int. Cl.
*G01J 3/00* (2006.01)
*G01J 3/28* (2006.01)

(52) U.S. Cl.
CPC ............ *G01J 3/28* (2013.01); *G01J 2003/283* (2013.01); *G01J 2003/2866* (2013.01)

(58) Field of Classification Search
CPC ........ G01J 3/02; G01J 3/28; G01J 3/42; G01J 3/46; G01J 3/50; G01J 3/51; G01J 3/52; G01N 21/31; G01N 21/552
See application file for complete search history.

(56) References Cited

U.S. PATENT DOCUMENTS

| 6,029,115 | A | * | 2/2000 | Tracy | ........................ | G01J 3/28 356/319 |
|---|---|---|---|---|---|---|
| 6,178,002 | B1 | | 1/2001 | Mueller-Wirts | | |
| 7,450,340 | B2 | | 11/2008 | Lee et al. | | |
| 7,586,094 | B2 | | 9/2009 | Liu et al. | | |
| 8,358,417 | B2 | | 1/2013 | Feitisch et al. | | |
| 2005/0236563 | A1 | | 10/2005 | Busch et al. | | |

(Continued)

FOREIGN PATENT DOCUMENTS

DE 19743493 C2 2/2001
WO WO-2012/054886 A1 4/2012

OTHER PUBLICATIONS

Benoy, et al. "Recovery of Absorption Line Shapes With Correction for the Wavelength Modulation Characteristics of DFB Lasers." *IEEE Photonics Journal* 8.3 (2016): 1-17. IEEE. Accessed on Nov. 3, 2016. http://ieeexplore.ieee.org/stamp/stamp.jsp?tp=&arnumber=7464820&isnumber=7457727.

(Continued)

*Primary Examiner* — Abdullahi Nur
(74) *Attorney, Agent, or Firm* — Mintz Levin Cohn Ferris Glovsky and Popeo, P.C.

(57) ABSTRACT

A frequency registration deviation is quantified for a field spectrum collected during analysis by a spectroscopic analysis system of a sample fluid when the spectroscopic analysis system has deviated from a standard calibration state. The field spectrum is corrected based on the frequency registration deviation using at least one spectral shift technique, and a concentration is calculated for at least one analyte represented by the field spectrum using the corrected field spectrum. Related systems, methods, and articles are described.

23 Claims, 12 Drawing Sheets

(56) References Cited

U.S. PATENT DOCUMENTS

2007/0229821 A1  10/2007  Christian et al.
2013/0250301 A1   9/2013  Feitisch et al.
2015/0142364 A1   5/2015  Workman

OTHER PUBLICATIONS

Ozdemir, D. et al. "Effect Of Wavelength Drift On Single-And Multi-Instrument Calibration Using Genetic Regression." *Applied Spectroscopy*, The Society For Applied Spectroscopy. Baltimore, US, vol. 52, No. 9, Sep. 1, 1998 (Sep. 1, 1998), pp. 1203-1209. XP000779129, ISSN: 0003-7028, DOI: 10.1366/0003702981945020. Abstract p. 1204.

Xiang, Liu. "Line-Of-Sight Absorption Of H20 Vapor: Gas Temperature Sensing In Uniform And Nonuniform Flows." Jun. 1, 2006 (Jun. 1, 2006). XP055328262 pp. 77-106.

* cited by examiner

DETERMINATION AND CORRECTION OF FREQUENCY REGISTRATION DEVIATIONS FOR QUANTITATIVE SPECTROSCOPY

TECHNICAL FIELD

The subject matter described herein relates to spectroscopic analysis in general, and more specifically to approaches for achieving and maintaining accurate and reproducible frequency and/or wavelength registration of absorbance spectral data from a spectroscopic analyzer.

BACKGROUND

One or more of degradation, drift, or non-reproducibility of hardware of a spectroscopic analysis system can affect frequency and wavelength registration and therefore the accuracy and reproducibility of measurements made using such a system. These effects are generally inevitable in real-world applications of spectroscopic analysis. Hardware of a spectroscopic analysis system can include light sources (e.g. lamps, lasers, or the like), electronics, optics, mechanical components, and the like. Achieving and maintaining accurate and reproducible frequency and wavelength registration of absorbance spectral data can be an important consideration in quantitative spectroscopy.

Currently available approaches to addressing these issues have included reference cell technologies that use in-line or split beam path configurations, periodic checks of frequency and/or wavelength registration using validation gas or gas mixtures, and peak tracking of one or more strong spectral peaks of a target analyte and/or another "background" compound present in a sample fluid to correct for frequency registration deviations. However, reference or validation cells (e.g., as described in co-owned U.S. Pat. No. 8,358,417, which is incorporated herein by reference) can require additional hardware installation and potentially add complexity to analytical system design. Periodic frequency or wavelength registration checks using one or more standard gases or gas mixtures generally require switching mechanisms for a fluid (e.g. gas or liquid) containing a known concentration of the target analyte or another compound (which may or may not be present in the process sample fluid) that absorbs light in the target wavelength region, in addition to a supply of the consumable standardized fluid. This approach also interrupts continuous process measurements, which can lead to significant measurement blind time while performing system validations. Peak tracking approaches can be susceptible to background fluid composition changes as well as temperature and pressure effects. Additionally, while peak tracking generally can be used to correct linear frequency registration deviation, it typically provides fewer benefits in correcting for non-linear frequency registration deviation.

SUMMARY

In one aspect, a method includes quantifying a frequency registration deviation for a field spectrum collected during analysis by a spectroscopic analysis system of a sample fluid when the spectroscopic analysis system has deviated from a standard calibration state. The field spectrum is corrected based on the frequency registration deviation using at least one spectral shift technique, and a concentration is calculated for at least one analyte represented by the field spectrum. The calculating includes applying the set of calibration algorithms to the corrected field spectrum.

In one aspect, a method includes quantifying a frequency registration deviation for a field spectrum collected during analysis by a spectroscopic analysis system of a sample fluid when the spectroscopic analysis system has deviated from a standard calibration state, correcting the field spectrum based on the frequency registration deviation using at least one spectral shift technique, and calculating a concentration for at least one analyte represented by the field spectrum using the corrected field spectrum.

In optional variations, one or more of the following features can be included in any feasible combination. For example, in some implementations the spectroscopic analysis system can optionally include at least one of a laser light source and a non-laser light source disposed to cause a beam of light to pass through the sample fluid at least once, and a detector to quantify the field spectrum. In an implementation in which the spectroscopic analysis system includes the laser light source, the laser light source can optionally include one or more of a semiconductor laser, a tunable diode laser, a quantum cascade laser, an intraband cascade laser, a horizontal cavity emitting laser, a vertical cavity surface emitting semiconductor laser, a distributed feedback laser, a distributed Bragg reflector laser, an external cavity tuned semiconductor laser, a gas discharge laser, a liquid laser, and a solid laser. In an implementation in which the spectroscopic analysis system includes the non-laser light source, the non-laser light source can optionally include one or more of a light emitting diode, an incandescent source, a thermal source, a discharge source, a laser assisted source, a laser driven plasma source, a fluorescent source, a super-luminescent source, an amplified spontaneous emission (ASE) source, a super-continuum source, a spectrally broad source, and a widely tunable QCL source with a tunable grating type waveguide filter.

The spectroscopic analysis system can optionally further include a sample cell to contain the sample fluid while the beam of light passes through the sample fluid at least once. Alternatively, the spectroscopic analysis system can optionally further include a free space volume in which the sample fluid is positioned while a beam of light passes through the sample fluid at least once. The quantifying of the frequency registration deviation for the field spectrum can optionally include applying a set of calibration algorithms to the field spectrum, and/or the quantifying of the frequency registration deviation for the field spectrum can optionally include using at least one frequency registration deviation function included in a set of calibration algorithms.

The set of calibration algorithms can optionally include a concentration function for the spectroscopic analysis system, and the quantifying can optionally include mathematically altering a frequency registration deviation of the field spectrum to create a predetermined number of variations, calculating one or more confidence indicators for each variation of the field spectrum after applying the concentration function to all variations of the field spectrum, and modeling each confidence indicator or a combination of more than one confidence indicator as a single-variate function of frequency registration deviation to mathematically determine an optimum frequency registration deviation that minimizes or maximizes the confidence indicator or combination of more than one confidence indicator. The concentration function can optionally be based on an unmodified calibration spectral data set that does not include artificially generated frequency registration deviation spectra. The calculating of the concentration for the analyte can optionally include applying the concentration function to the field spectrum variation that corresponds to the optimum frequency registration deviation.

The set of calibration algorithms can optionally include an output of a calculation engine based on multivariate analysis of a set of calibration data representative of the standard calibration state of the spectroscopic analysis system. The set of calibration data can optionally include artificially generated frequency registration deviation spectra generated at design time by applying mathematical shifts to calibration spectra collected using calibration samples. The quantifying of the frequency registration deviation for the field spectrum can optionally include applying the set of calibration algorithms to calculate a characteristic indicator of frequency registration for the field spectrum and quantifying the frequency registration deviation for the field spectrum by comparing the characteristic indicator with a measured indicator of frequency registration determined from the field spectrum. The measured indicator of frequency registration can optionally include one or more spectral features and/or a spacing between the one or more spectral features.

The correcting can optionally include correcting the field spectrum based on a quantified measurement state frequency registration deviation using the at least one spectral shift technique. The at least one spectral shift technique can optionally include at least one of a linear shift, a nonlinear shift, a stretch of the measured spectrum, and a compression of the measured spectrum. The at least one spectral shift technique can optionally be applied in one or more of a purely mathematical manner, via hardware tuning, and by using a combination of mathematical corrections and hardware tuning. The at least one spectral shift technique can optionally be applied to the entire field spectrum or to one or more individual sections of the field spectrum.

Systems and methods consistent with this approach are described as well as articles that comprise a tangibly embodied machine-readable medium operable to cause one or more machines (e.g., computers, etc.) to result in operations described herein. Similarly, computer systems are also described that may include computer hardware, such as for example one or more processors and a memory coupled to the one or more processors. The memory may include one or more programs that cause the one or more processors to perform one or more of the operations described herein.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Consistent with implementations of the current subject matter, multivariate analysis approaches as described herein can be used to model and correct for frequency registration deviation effects that can occur in a spectroscopic analysis system, without requiring changes to the existing hardware of the spectroscopic analysis system, periodic (or non-periodic) instrument validations using standard gases, or reliance on peak tracking of compounds in a fluid sample. In this manner, robust, reliable, and reproducible measurements can be achieved and maintained.

While example implementations of the current subject matter are described herein in relation to harmonic spectroscopy techniques using a wavelength or frequency modulated tunable diode laser absorbance spectrometer (TDLAS) or tunable semiconductor laser spectrometer, it will be understood that approaches consistent with the current subject matter can be used in conjunction with analytical instrumentation or methods relating to any quantitative spectroscopic approach, including but not limited to absorption, emission and fluorescence spectroscopy, such as, for example, Fourier transform infrared (FTIR) spectroscopy, non-dispersive infrared (NDIR) spectroscopy, cavity enhanced spectroscopy (CES), cavity ring-down spectroscopy (CRD), integrated cavity output spectroscopy (ICOS), photoacoustic spectroscopy, Raman spectroscopy, and the like.

Figure 1:
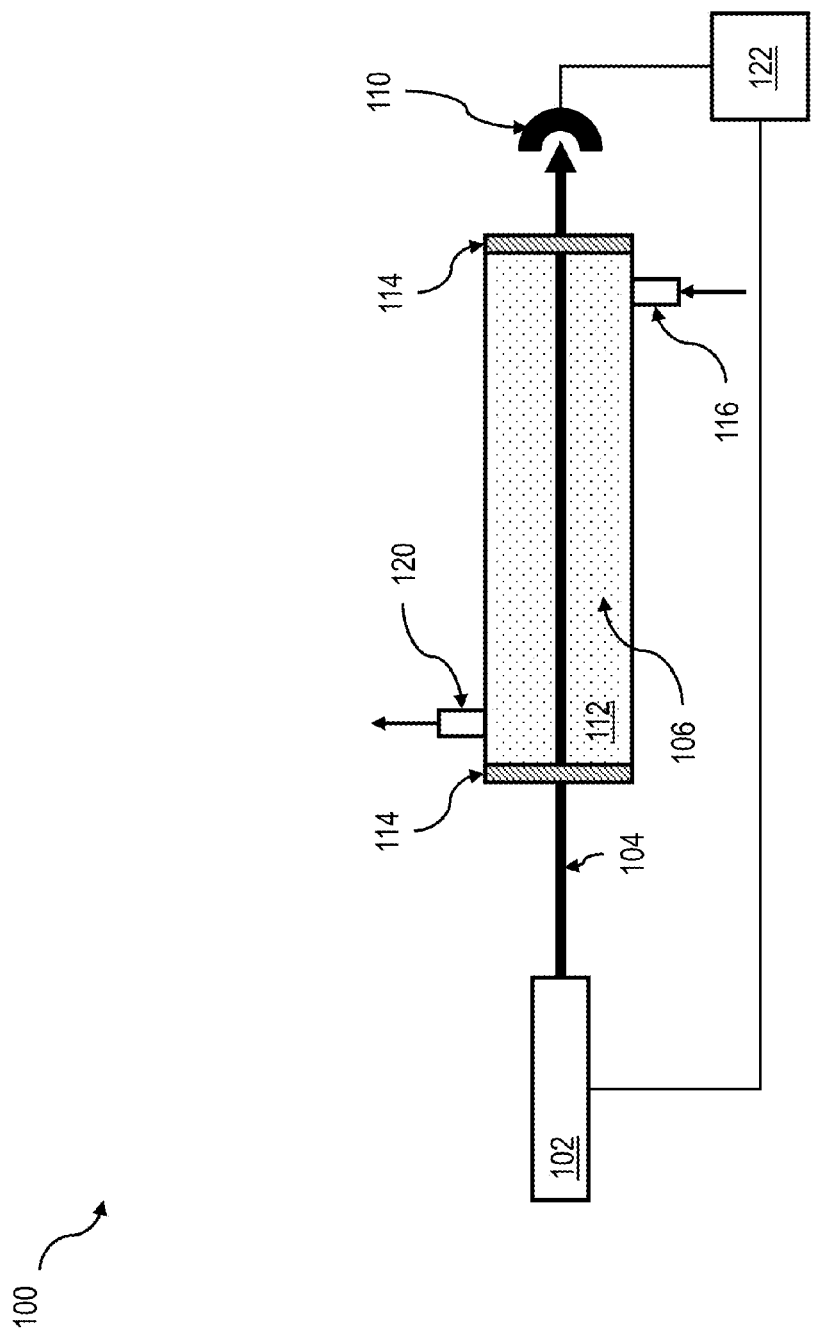
FIG. 1 shows a diagram illustrating an example of a spectroscopic measurement system.

FIG. 1 shows a diagram of an example spectroscopic analysis system 100, which includes features that may appear in other spectroscopic analysis systems consistent with implementations of the current subject matter. The spectroscopic analysis system 100 can include a light source 102 operating at one or more target wavelengths or over a range of wavelengths. The light source 102 provides a continuous beam or pulses of radiation (e.g. light in the visible, ultraviolet, infrared, or the like, or other types of electromagnetic radiation) projected along a light path 104 that passes through a volume 106 of a sample fluid before being detected by a detector 110. The light source 102 can optionally include one or more lasers, for example a semiconductor laser, a tunable diode laser (TDL), a quantum cascade laser (QCL), an intraband cascade laser (ICL), a horizontal cavity emitting laser (HCSEL), a vertical cavity surface emitting semiconductor laser (VCSEL), a distributed feedback laser (DFB), a distributed Bragg reflector laser (DBR), an external cavity tuned semiconductor laser, a gas discharge laser, a liquid laser, a solid laser, and the like. The light source 102 can also or alternatively include one or more non-laser light sources, such as for example a light emitting diode (LED), a lamp, and/or another device capable of generating frequency tunable light through nonlinear optical interactions and/or through spectral filtering. Examples of lamps can include, but are not limited to thermal sources, discharge sources, laser assisted or laser driven plasma sources, fluorescent sources, super-luminescent sources, amplified spontaneous emission (ASE) sources, super-continuum sources, and spectrally broad sources. Also included within the scope of the current disclosure are examples such as widely tunable QCL sources with tunable grating type waveguide filters (e.g. those available from Redshift Systems of Burlington, Mass.).

The detector 110 can include one or more of a photodiode, a photodetector, a photoacoustic detector, or other devices or structures for detecting an intensity of the radiation emitted by the light source 102 after the path has passed at least once through the volume 106. In some implementations, the volume 106 can be contained in a sample cell 112 having one or more windows or other openings 114 through which the light path 104 passes into and out of the volume 106. The sample cell 112 can be a flow through cell as shown in FIG. 1, in which fluid flows into the sample cell 112 via an inlet 116 and out of the sample cell 112 through an outlet 120. In still other implementations of the current subject matter, an analytical system can omit a sample cell and can instead be configured such that the light path passes at least once through an open (e.g. unbounded or unenclosed) space (e.g. within a stack, in the open atmosphere, etc.) in traversing between the light source 102 and the detector 110. In an open path system consistent with this implementation, the light path can optionally include one or more reflections via mirrors or other reflective surfaces arranged within or adjacent to the open space volume.

Other configurations are possible besides that shown in FIG. 1. For example, a path length of the light path 104, which is the distance the continuous beam or pulses of radiation travels through the sample fluid, can be established using mirrors, beam splitters, or by varying other geometrical parameters such as the location of the light source 102 and/or the detector 110. Furthermore, the sample volume can contain a non-enclosed open path between the light source 102 and the detector 110. Depending on the analyte or analytes to be measured, the concentration range over which one or more analytes are expected to be present, and the presence of other compounds or materials that might interfere with the accuracy of a measurement in the sample, the continuous beam or pulses of light can be projected through free fluid (such as for example in a pipeline, an exhaust stack, etc.) or even free air or liquid (such as for example in the open atmosphere, a body of water, etc.). Alternatively, a batch volume 106 of sample fluid can be analyzed in a sample cell 112, for example one such as that shown in FIG. 1 with additional conduits or tubing, valves, and/or vacuum or pumping equipment to deliver a first batch volume 106 and to subsequently remove that first batch volume from the sample cell 112 to prepare for analysis of a second batch volume. A controller 122 can be incorporated to receive and analyze the detector data from the detector 110, to control the light source 102, and optionally to perform one or more of the operations discussed below in relation to virtual reconstruction of a calibration state of the spectroscopic analysis system 100.

Modulation spectroscopy, which is also referred to as harmonic spectroscopy, is a widely used technique for sensitive detection of analyte(s) at very low concentrations (e.g. in the sub-parts-per-million or sub-parts-per-billion range). In modulation spectroscopy, the wavelength and/or the amplitude of the light source 102 is modulated at a modulation frequency f. Light emitted by the laser light source 102 is passed through the sample gas 106 over a path length. The intensity of the continuous beam or pulses of light 104 as it impinges on the detector 110 can optionally vary in amplitude. Fourier analysis of the signal generated by the detector 110 includes signal components at the modulation frequency f as well as at harmonic frequencies at multiples of the modulation frequency f (e.g. 2f, 3f, 4f, etc.). Demodulation of one of the harmonic frequencies, for example the 2f, yields a signal that can be used to very accurately determine the concentration of one or more analytes in the sample fluid 106. By shifting phase-sensitive detection to higher frequencies, modulation spectroscopy can significantly reduce 1/f noise and achieve high sensitivity. Modulation spectroscopy can be highly sensitive for detecting and quantifying low analyte concentrations, and an analyte concentration can be quantified directly from the demodulated signal from the detector 110. Additionally, a lock-in amplifier or other signal filtering processes or devices can be used to isolate absorbance signals due to the analyte from background drift or other noise in the instrument. Other spectroscopic approaches can include one or more of these and optionally other features or processes.

The term spectral data refers to data quantifying one or more of an absorbance, a reflectance, a fluorescence, a scattering, or an emission occurring in response to incident light interacting with molecules of a sample fluid such as a gas or a liquid in a spectroscopic analysis system. Terms used in this disclosure in describing changes to spectroscopic analysis system performance that can occur as a result of hardware variations over time include frequency registration (FR), which refers to an alignment of a frequency axis (commonly the x-axis) of spectral data; frequency registration deviation (FRD), which refers generally to any changes or deviations to the frequency axis of spectral data obtained from a spectroscopic analysis system; and an indicator of frequency registration (IFR), which refers to one or more spectral features (e.g. a peak, a valley, a zero crossing point, an inflection point, or another characteristic point) in the spectral data, and/or the spacing between defined or chosen spectral features.

Spectral data refers to one or more sets of spectroscopic data collected using a spectroscopic analysis system. Field spectral data refers to spectroscopic data collected using a spectroscopic analysis system to analyze one or more field samples, while calibration spectral data refers to spectroscopic data collected using a spectroscopic analysis system to analyze one or more calibration samples. Field sample is a term used herein to refer to a fluid (e.g. gas or liquid) containing an unknown quantity of one or more analytes of interest, while a calibration sample is one for which one or more analyte concentrations are known or well characterized. An analyte refers generally to an element or a compound having one or more spectral features for which the spectroscopic analysis system is configured to capture spectral data. A spectral measurement state refers to a state of the hardware of the spectroscopic analysis system at the time that spectral data are collected.

A calibration state refers to a state of the hardware of the spectroscopic analysis system when the spectroscopic analysis system is calibrated, for example when calibration spectral data are collected. Calibration spectral data refer to spectral data collected using a spectroscopic analysis system to analyze one or more calibration samples having a known or well-characterized amount of an analyte or some other element or compound and optionally one or more other known or well-characterized measurement parameters, such as for example temperature, pressure, a background composition of the calibration sample, etc. A function, as used herein, refers to a mathematical operation or set of mathematical operations that result in a transformation of a set of data. An example of a function is a vector or matrix that includes values that mathematically operate on a spectral data set.

Regardless of the spectroscopy technique used, an approach consistent with the current subject matter generally involves one or more calibration models and/or calibration algorithms built in the factory using one or more sets of calibration spectral data. Such calibration spectral data can be advantageously designed to be mathematically representative of concentration ranges expected to be encountered for field samples analyzed using the spectroscopic analysis system. The quantitative characteristics of field samples, including but not limited to one or more analyte concentrations (e.g. partial pressure, mole fraction, mass or number of moles per volume, volume ratio, or the like), sample pressure, sample temperature, flow rate, viscosity, etc., can be calculated or predicted by applying the one or more calibration models to measured field sample spectra. Unless otherwise specified or otherwise inconsistent with the context in which it appears, the term concentration is used generically to refer to any of the possible quantitative characteristics listed above. The frequency registration deviation of a spectral measurement state generated by a spectroscopic analysis system can be quantified using approaches similar to those described herein. This quantified frequency registration deviation can be used to correct a current spectral measurement state to best emulate an original calibration state of the system, based on which a concentration can be calculated.

In some advantageous implementations of the current subject matter, a universally-accepted standard calibration state for a spectroscopic analysis system can be established and recorded. For example, this standard calibration state can be characterized at a factory or assembly facility at which the spectroscopic analysis system is manufactured, a testing facility, etc., and can be defined for multiple individual units of a factory-standard spectroscopic analysis system. A subsequent measurement state of any spectroscopic analysis system with the same relevant technical specifications can be referenced to this standard calibration state, thus tying together the calibration state of the similar spectroscopic analysis systems. The frequency registration deviation correction can be used on a single spectroscopic analysis system operating in the field to correct its measurement state. In addition or alternatively, a frequency registration deviation correction can be used on a more universal level for correcting the calibration state of multiple comparable instances of a spectroscopic analysis system to the standard calibration state.

Further advantages that can be realized with implementations of the current subject matter can include real time measurement state correction that allows for a more robust system. Such measurement state corrections can reduce or eliminate susceptibility to hardware degradation, drift and/or non-reproducibility, thereby assisting in maintaining the fidelity of the quantitative measurements. System lifetime of instruments in the field can also be increased, and customer returns reduced.

A calibration model such as those described herein can be built and the frequency registration deviation can be quantified and corrected using various multivariate analysis methods that include, but are not limited to, classical least square regression (CLS), inverse least square regression (ILS), principal component analysis (PCA), principal component regression (PCR), partial least square regression (PLS), multiple linear regression (MLR), etc. The quantification can be applied to an entire measured spectrum or to one or more individual sections of the measured spectrum as well as sample pressure and temperature data, or other relevant measurement data. These multivariate techniques can be applied by a calculation engine embedded in the spectroscopic analysis system or by standalone commercially available software, for example executing on one or more general purpose computers.

The correction of a frequency registration deviation for a spectroscopic analysis system can include one or more spectral shift correction techniques, such as for example a linear shift, a nonlinear shift, a stretch of the measured spectrum, a compression of the measured spectrum, etc. These corrections can be applied either in a purely mathematical manner (e.g. by performing a mathematical transformation on a collected field sample spectrum), via hardware tuning (which can optionally include but is not limited to, adjustments to one or more of a laser operating temperature, a laser operating current (e.g. a nominal current value and/or a current ramp rate), a laser modulation current, a demodulation phase, a detection phase, a modulation frequency, a modulation frequency, a detection gain, or the like), or using a combination of mathematical corrections and hardware tuning. The correction can be applied to the entire or individual sections of a measured field sample spectrum.

Figure 2:
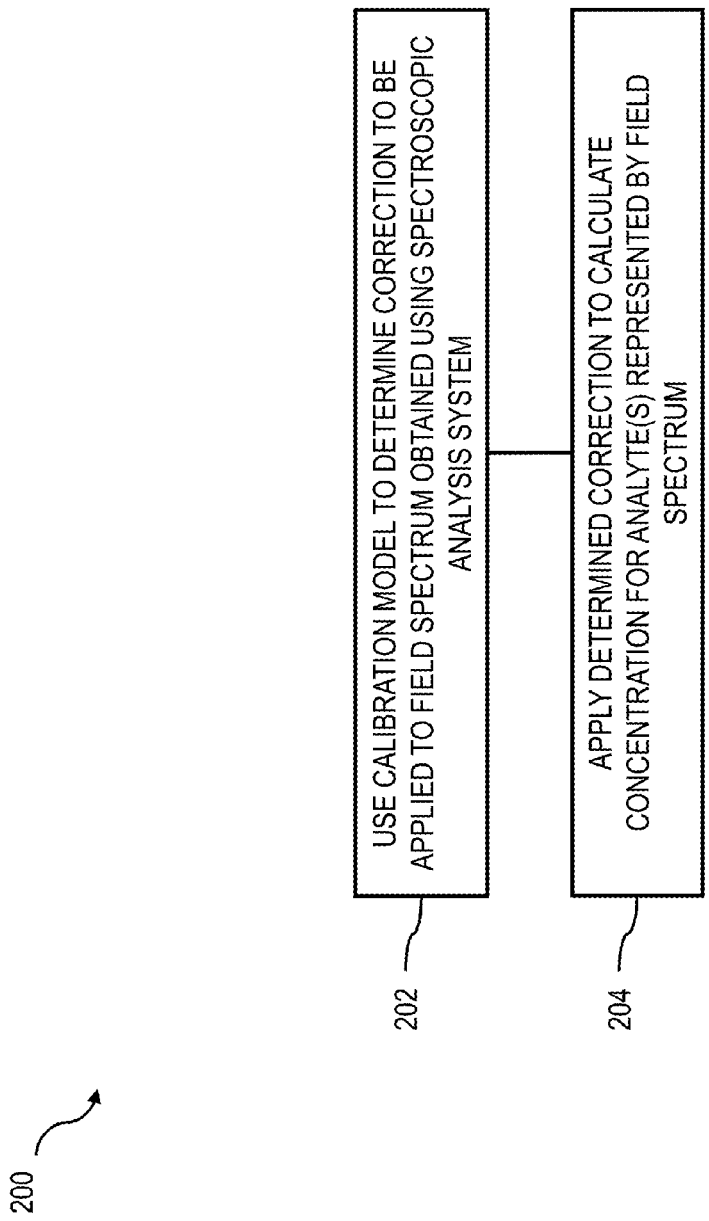
FIG. 2 shows a process flow diagram illustrating method features consistent with implementations of the current subject matter.

In general, calculations of analyte concentrations can be improved in accordance with implementations of the current subject matter through a process in which a pre-determined calibration model for a spectroscopic analysis system is used in quantifying a frequency registration deviation and applying a correction to a field spectrum. As discussed in greater detail below, the calibration model can include a set of calibration algorithms, which can optionally be based on a calibration data set collected using the spectroscopic analysis system. Alternatively or in addition, the calibration model can include a concentration function generated by a calculation engine using a null calibration set as input. FIG. 2 shows a process flow chart illustrating features of a method consistent with the current subject matter. At 202, such a method includes use by the spectroscopic analysis system of the calibration model to determine a correction to be applied to a field spectrum obtained using the spectroscopic analysis system. The correction compensates or otherwise corrects for a frequency registration deviation that has occurred for the spectroscopic analysis system relative to a previous calibration state. This correction is then applied at 204 to calculate a concentration of one or more analytes having spectral features captured in the field spectrum. The following descriptions of implementations of the current subject matter include details relating to one or more of these more general features.

Figure 3:
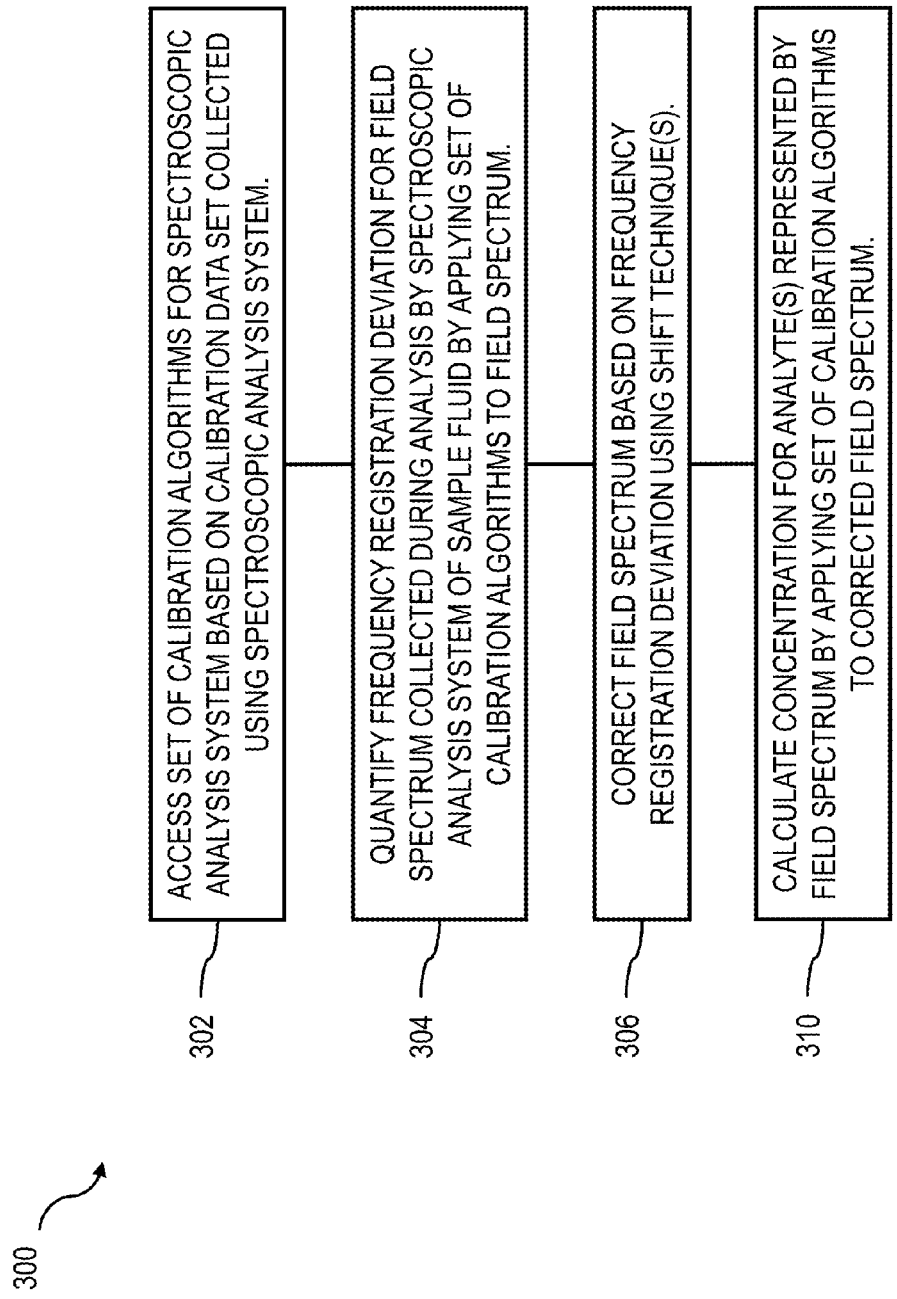
FIG. 3 shows another process flow diagram illustrating method features consistent with implementations of the current subject matter.

FIG. 3 shows a process flow chart illustrating features of a method 300 consistent with implementations of the current subject matter. At 302, the method 300 includes accessing the calibration model, which in this example can include a set of calibration algorithms for a spectroscopic analysis system that are based on a multivariate analysis of a calibration spectral data set. The accessing of one or more calibration models, algorithms, functions, etc. referred to in this disclosure can generally indicate that a processor or other computer hardware, which can optionally be part of a spectroscopic analysis system or alternatively a remote computing system or systems that is or are configured to exchange data with the spectroscopic analysis system, is prepared to execute the other processes discussed. In some examples, the accessing can include reading the one or more calibration models, algorithms, functions, etc. from a local computer or machine-readable storage device or alternatively can include receiving this information over a network or other data connection from a remote system. It will be understood that accessing of the one or more calibration models, algorithms, functions, etc. is not essential as the processor or other computer hardware performing the various calculations and corrections can be pre-loaded with the calibration models, algorithms, functions, etc., either at design time or at start-up, etc.

The calibration spectral data set can be collected by using the spectroscopic analysis system to collect spectral data for a variety of known conditions, which can, in some implementations of the current subject matter, be selected from varying concentrations of one or more analytes, varying pressure or temperature, varying the concentration of one or more other compounds (besides the one or more target analytes), varying the laser operating current (e.g. the nominal current value and/or the current ramp rate), varying the laser operating temperature, or the like.

The set of calibration algorithms can include one or more models, or alternatively one or more matrices (e.g. vectors, sets of vectors, etc.), functions, algorithms, statistical tools, or the like that can be used in conjunction with field spectral data to predict either or both of an indicator of frequency registration and a frequency registration deviation of the spectroscopic analysis system at the time of collection of the field spectral data and also to predict a concentration of one or more analytes in the sample fluid for which the field spectrum was collected. The set of calibration algorithms are applied at 304 to a field spectrum collected by the spectroscopic analysis system for a sample fluid, thereby quantifying a frequency registration deviation for the field spectrum. The quantified frequency registration deviation can be used at 306 to correct the field spectrum using one or more spectral shifting techniques such as those discussed above. The method further includes calculating a concentration for the one or more analytes represented by the field spectrum at 310.

It will be understood from FIG. 3 and the accompanying description in the preceding paragraphs that the generating of the set of calibration algorithms can be a "design time" process, for example one that is performed at a factory or assembly location for a given spectroscopic analysis system. In some examples, the generation of the set of calibration algorithms can occur when a spectroscopic analysis system is first manufactured and before the spectroscopic analysis system is placed into service. Alternatively or in addition, the set of mathematical corrections can be generated as part of a recalibration process that occurs either at a recalibration or refurbishment facility, at the factory, in the field, etc. Additionally, as noted above, the set of calibration algorithms can optionally represent a standard calibration state of multiple physical instances of a given configuration of the spectroscopic analysis system and can be determined based on a different physical spectroscopic analysis system than the spectroscopic analysis system for which it is used.

Figure 4:
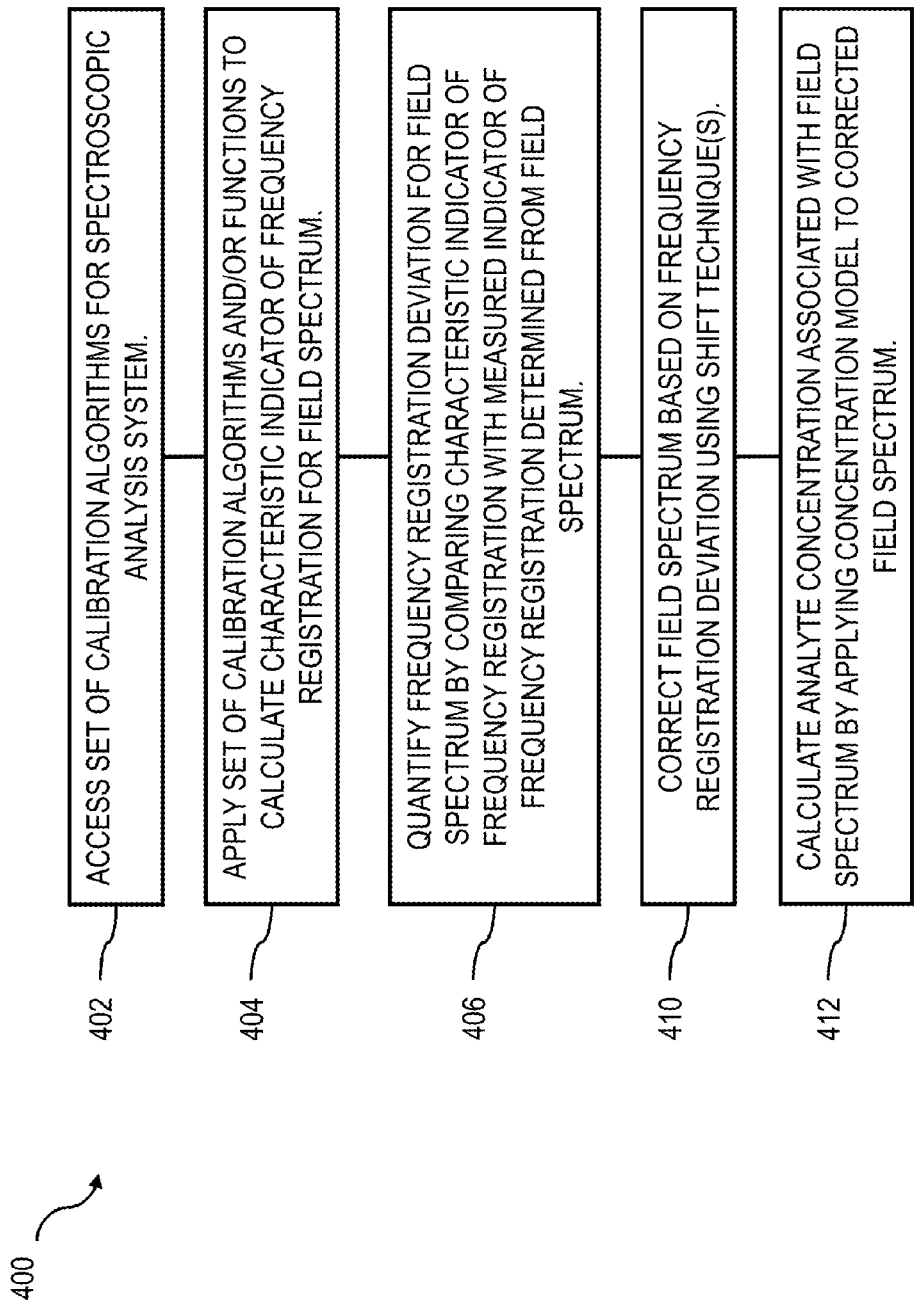
FIG. 4 shows another process flow diagram illustrating method features consistent with implementations of the current subject matter.
Figure 6:
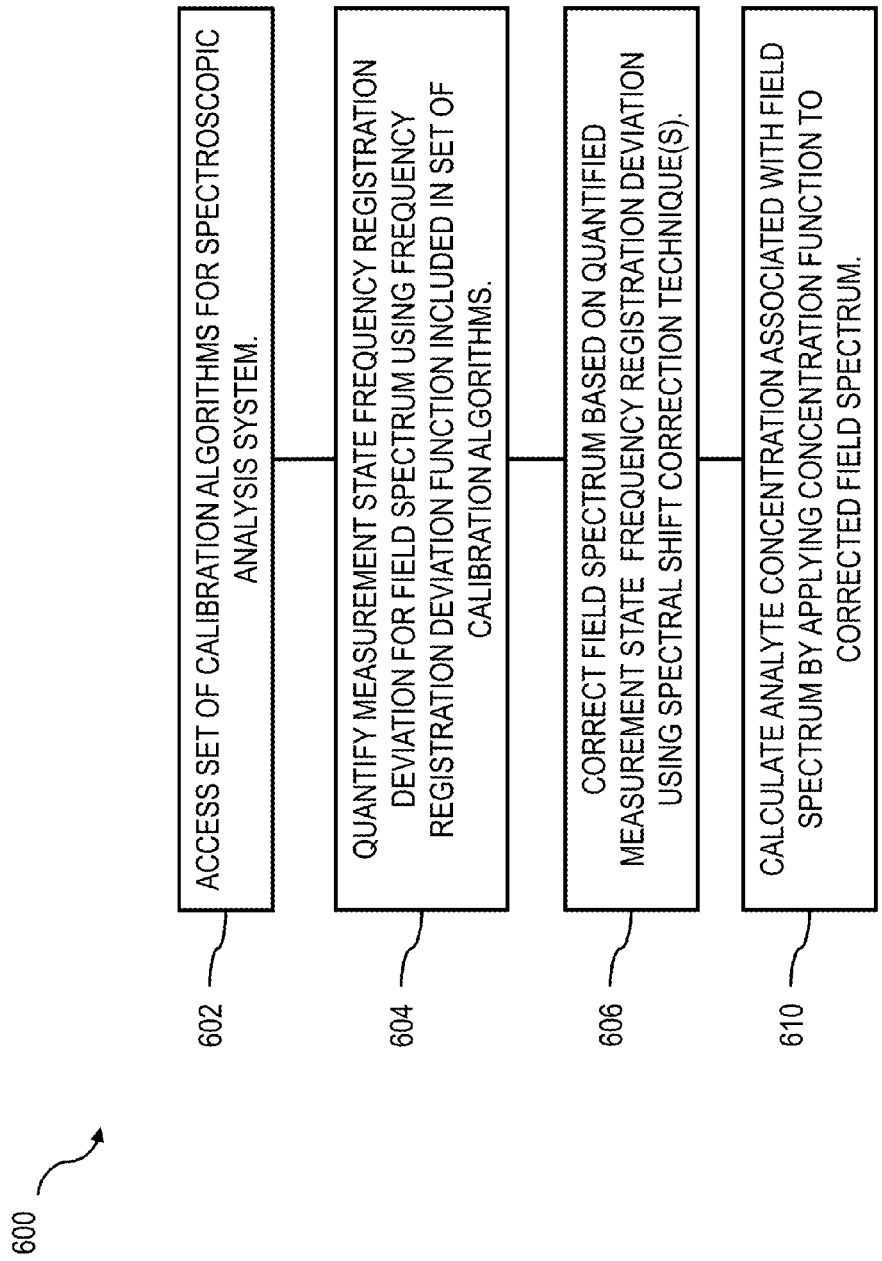
FIG. 6 shows another process flow diagram illustrating method features consistent with implementations of the current subject matter.
Figure 9:
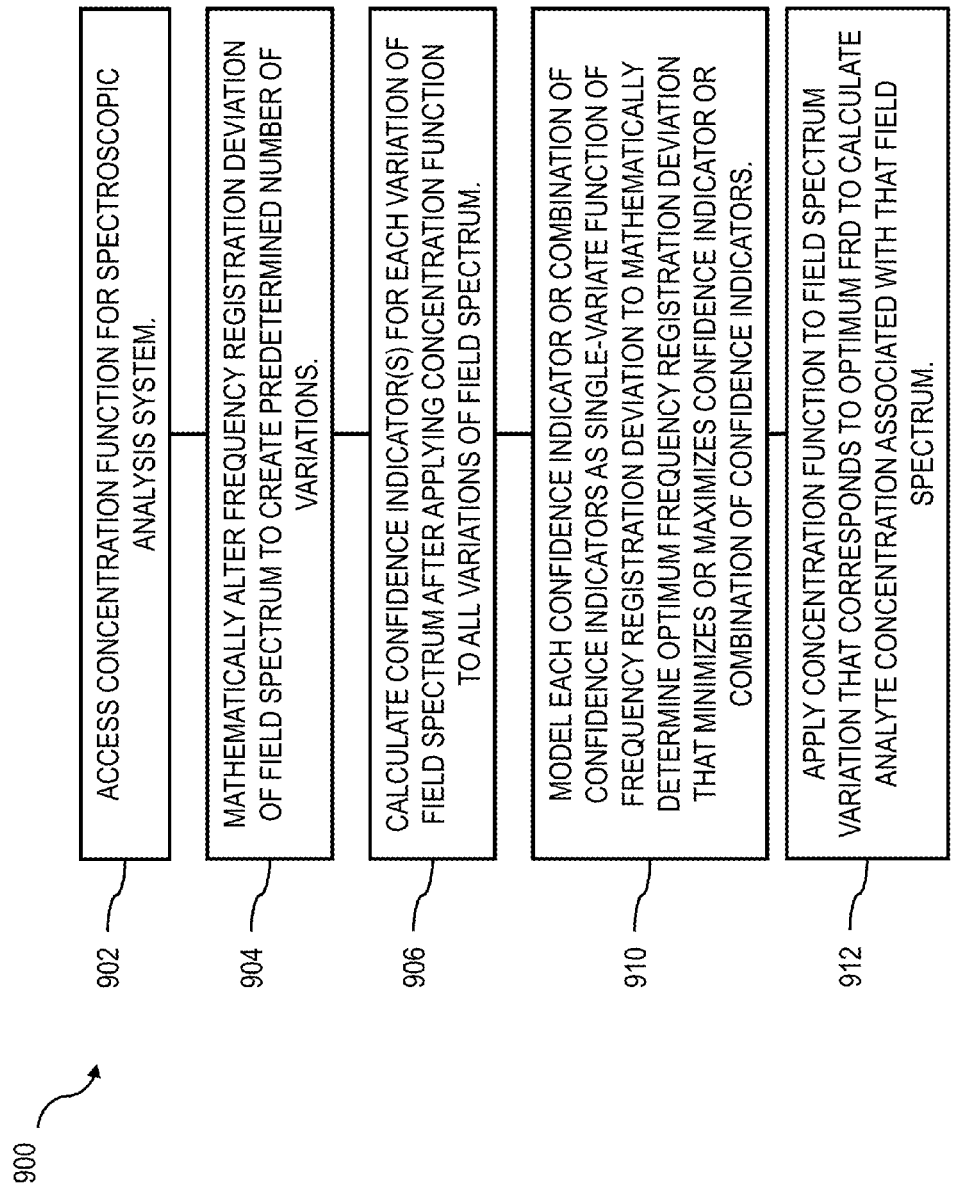
FIG. 9 shows another process flow diagram illustrating method features consistent with implementations of the current subject matter.

Various implementations of the current subject matter can include different approaches for generating the set of mathematical corrections and for the use of these mathematical corrections in predicting frequency registration deviation for a given field spectral data set collected by the spectroscopic analysis system. FIG. 4, FIG. 6, and FIG. 9 show process flow charts 400, 600, 900 illustrating features of methods consistent with some example approaches based on the generic approach explained above in reference to FIG. 2 and FIG. 3.

Figure 5:
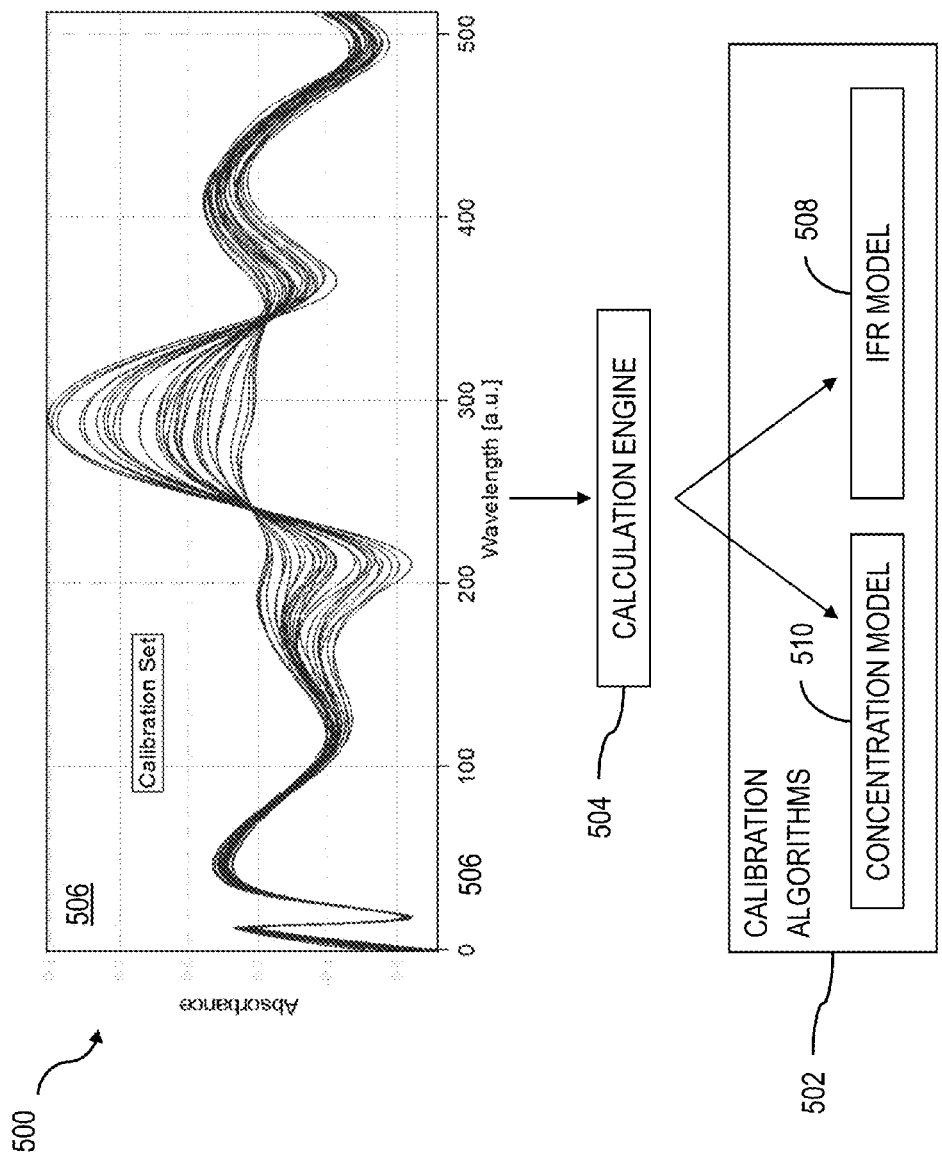
FIG. 5 shows a diagram illustrating features relating to generation of a set of calibration algorithms consistent with implementations of the current subject matter.

As shown in the process flow chart 400 of FIG. 4, in one approach, a computing device used for processing spectral data generated by a spectroscopic analysis system can access a set of calibration algorithms at 402. As noted previously, the processes leading to the creation of the set of calibration algorithms (discussed in further detail below in reference to FIG. 5) can be performed at design time and then loaded into memory or other computer-readable storage accessible by a spectroscopic analysis system controller 122 or other processor associated with a spectroscopic analysis system or otherwise receiving spectral data from a spectroscopic analysis system. As further illustrated in the diagram 500 of FIG. 5, the set of calibration algorithms 502 in this example are generated at design time using a calculation engine 504 based on inputs of an unmodified calibration spectral data set 506. The unmodified calibration spectral data set 506 can include a set of spectral data obtained through analysis of multiple samples over a chosen set of variations in one or more variables such as concentration, pressure, temperature, fluid flow rate, etc. No artificial or mathematical spectral shifts need to be applied to the unmodified calibration spectral data set 506 in this implementation.

The calculation engine 504 generates the set of calibration algorithms 502 optionally including either models or calibration functions relating to an indicator of frequency registration 508 and concentration 510. The calculation engine 504 can generate the set of calibration algorithms 502 based on a multivariate analysis of the unmodified calibration spectral data set 506, for example using CLS, PCA, PLS, etc. An indicator model for frequency registration can be used in predicting an indicator of frequency registration, and a concentration model can be used in calculating the concentration of one or more analytes in the field spectra data. Alternatively, the calibration algorithms can be based on a single model of the spectroscopic analysis system calibration state result. In such an approach, the calibration algorithms can be used to determine two calibration functions (e.g. calibration vectors, calibration matrices, etc.) for use in making frequency registration deviation predictions and concentration calculations, a first of which can be used in predicting an indicator of frequency registration for field spectral data, and a second of which can be used in calculating the concentration of one or more analytes in the field spectra data.

At 404, a characteristic indicator of frequency registration of field spectrum data collected for a field sample is calculated by applying the set of calibration algorithms 502. For example, the indicator of frequency registration model or the indicator of frequency registration calibration function discussed in the preceding paragraph can be applied to the field spectrum data. The characteristic indicator of frequency registration is compared with a measured indicator of frequency registration determined from the field spectrum to determine a frequency registration deviation for the spectroscopic analysis system at 406. This measured indicator of frequency registration can optionally be one or more spectral features and/or a spacing between the one or more spectral features. At 410, the field spectrum is corrected based on the frequency registration deviation using one or more spectral shift correction techniques as discussed above, and at 412, the concentration model is applied to the corrected field spectrum to calculate an analyte concentration associated with that field spectrum.

Figure 7:
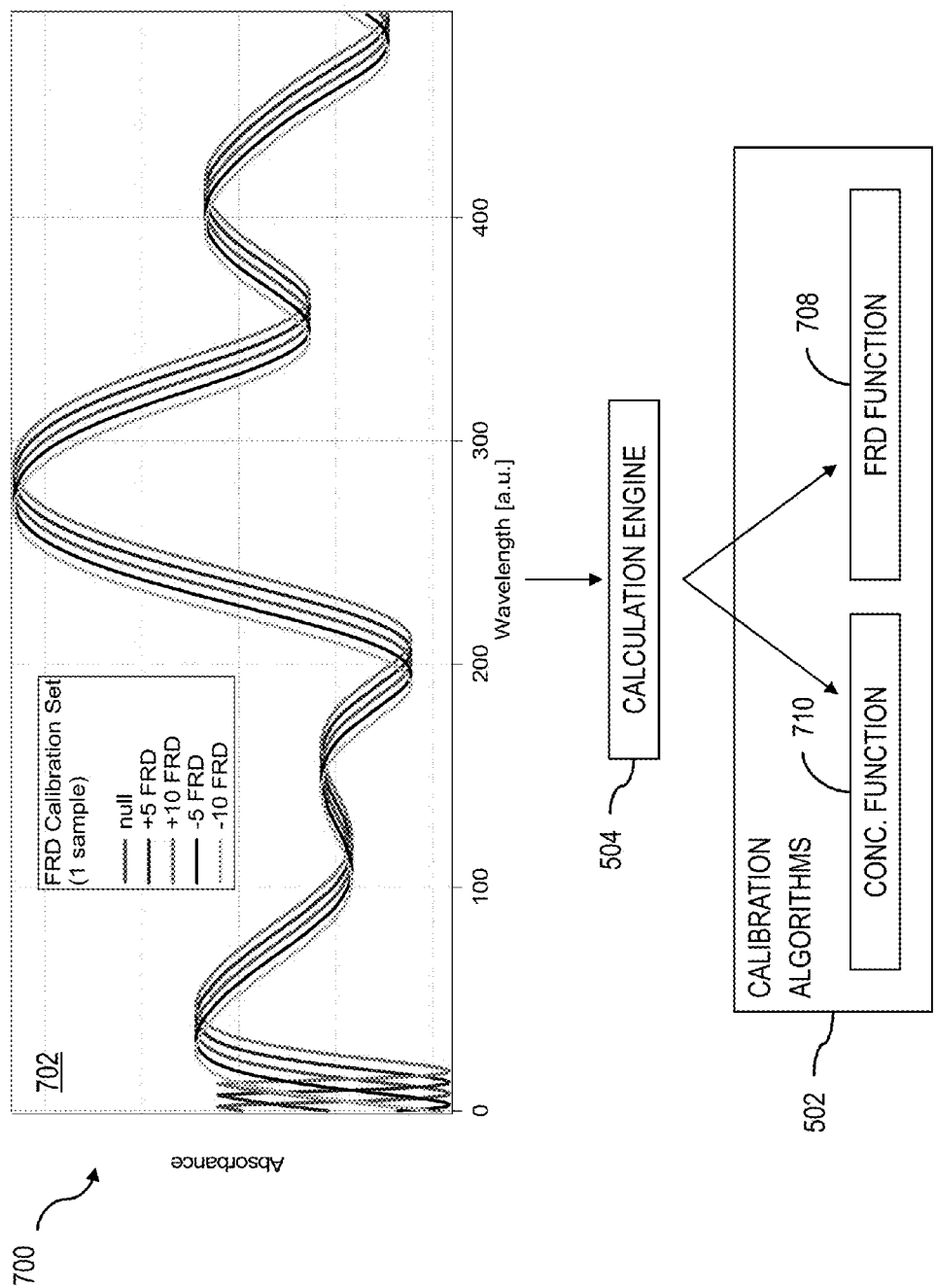
FIG. 7 shows a diagram illustrating features relating to generation of a set of calibration algorithms consistent with implementations of the current subject matter.

As with methods consistent with FIG. 4, the method illustrated in the process flow chart 600 of FIG. 6 can include a computing device used for processing spectral data generated by a spectroscopic analysis system accessing a set of calibration algorithms at 602. As noted previously, the processes leading to the creation of the set of calibration algorithms 502 can optionally be performed at design time and then loaded into memory or other computer-readable storage accessible by a spectroscopic analysis system controller 122 or other processor associated with a spectroscopic analysis system or otherwise receiving spectral data from a spectroscopic analysis system. As further illustrated in the diagram 700 of FIG. 7, the set of calibration algorithms 502 in this example are generated at design time using a calculation engine 504 based on inputs of a calibration spectral data set 702. In this example, however, the calibration spectral data set 702 includes artificially generated frequency registration deviation spectra and optionally also unmodified "null" calibration spectral data. The artificially generated frequency registration deviation spectra are generated by applying mathematical shifts to calibration spectra collected using calibration samples. The output of the calculation engine 504 is a model for the spectroscopic analysis system calibration state that can generate a set of calibration algorithms 502 including both of a frequency registration deviation prediction function 708 and a concentration calculation function 710.

Referring again to FIG. 6, at 604 the frequency registration deviation function 708 can be used to quantify a measurement state frequency registration deviation of a field spectrum collected by a spectroscopic analysis system. The field spectrum can be corrected at 606 based on this quantified measurement state frequency registration deviation, for example using one or more spectral shift correction techniques as discussed above. At 610, the concentration function 710 is applied to the corrected field spectrum to calculate an analyte concentration associated with that field spectrum.

Figure 8:
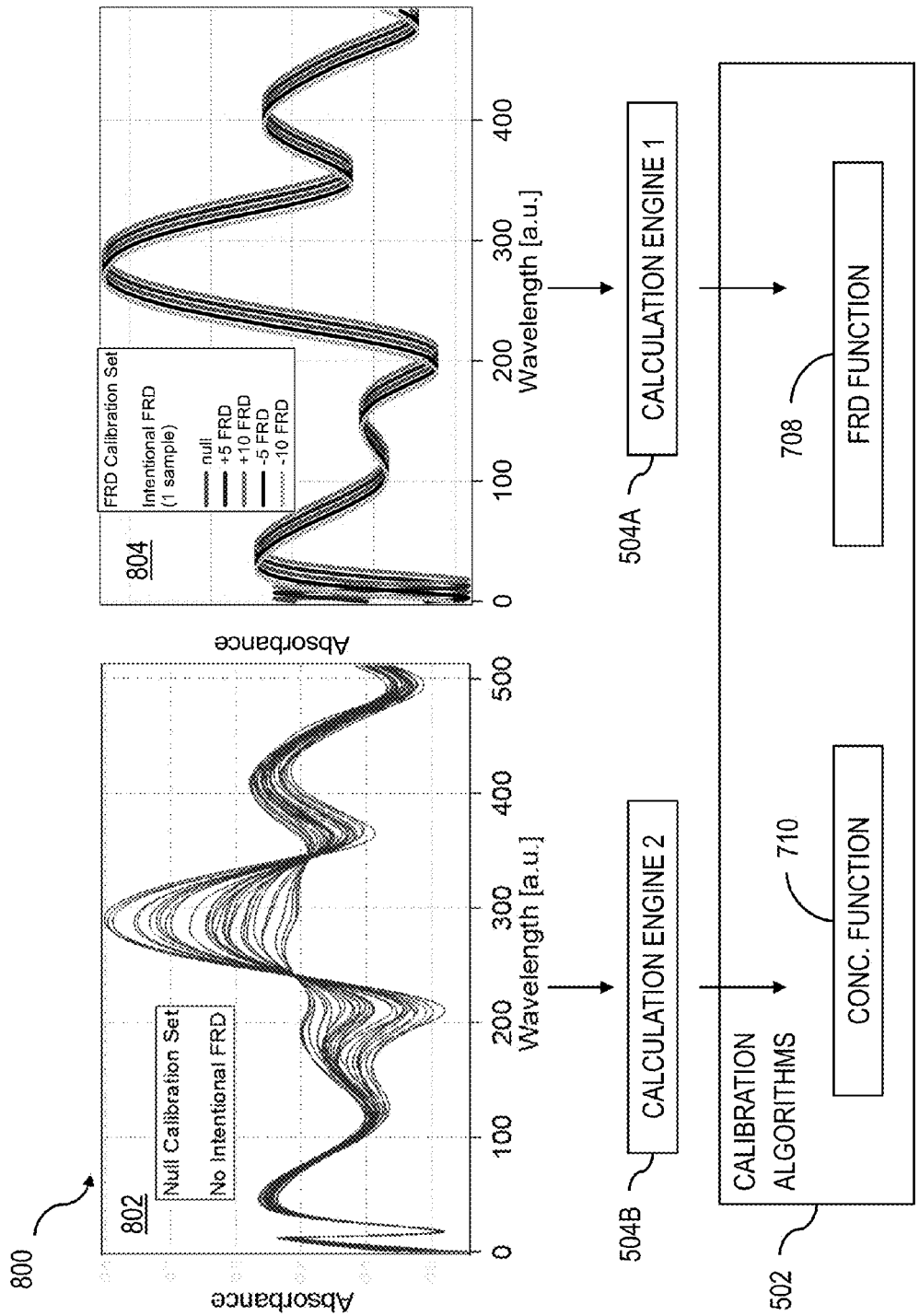
FIG. 8 shows a diagram illustrating features relating to generation of a set of calibration algorithms consistent with implementations of the current subject matter.

A method consistent with FIG. 6 can also be used in conjunction with a frequency registration deviation function 708 and a concentration function 710 generated as illustrated in the diagram 800 of FIG. 8. The set of calibration algorithms 502 in this example are generated at design time using a calibration engine 504 based on inputs of two calibration spectral data sets 802, 804. A first calibration spectral data set 802 includes an unmodified null calibration spectral data set that does not include artificially generated frequency registration deviation spectra. A second calibration spectral data set 804 includes both calibration spectra and artificially generated frequency registration deviation spectra generated by applying one or more of mathematical shifts and hardware tuning (e.g. any of performing a mathematical transformation on a collected calibration sample spectrum, adjusting a laser operating temperature, adjusting a laser operating current, adjusting a laser modulation current, adjusting a demodulation phase, adjusting a detection phase, either individually or in any combination) to calibration spectra collected using calibration samples. In this example, parallel calculation models 504A, 504B, or alternatively, a single calculation engine (not shown in FIG. 8) doing serial processing of the calculations required, generate a set of calibration algorithms 502 including a frequency registration deviation function 708 based on the second calibration spectral data set 804 and a concentration function 710 based on the first calibration spectral data set 802.

Figure 10:
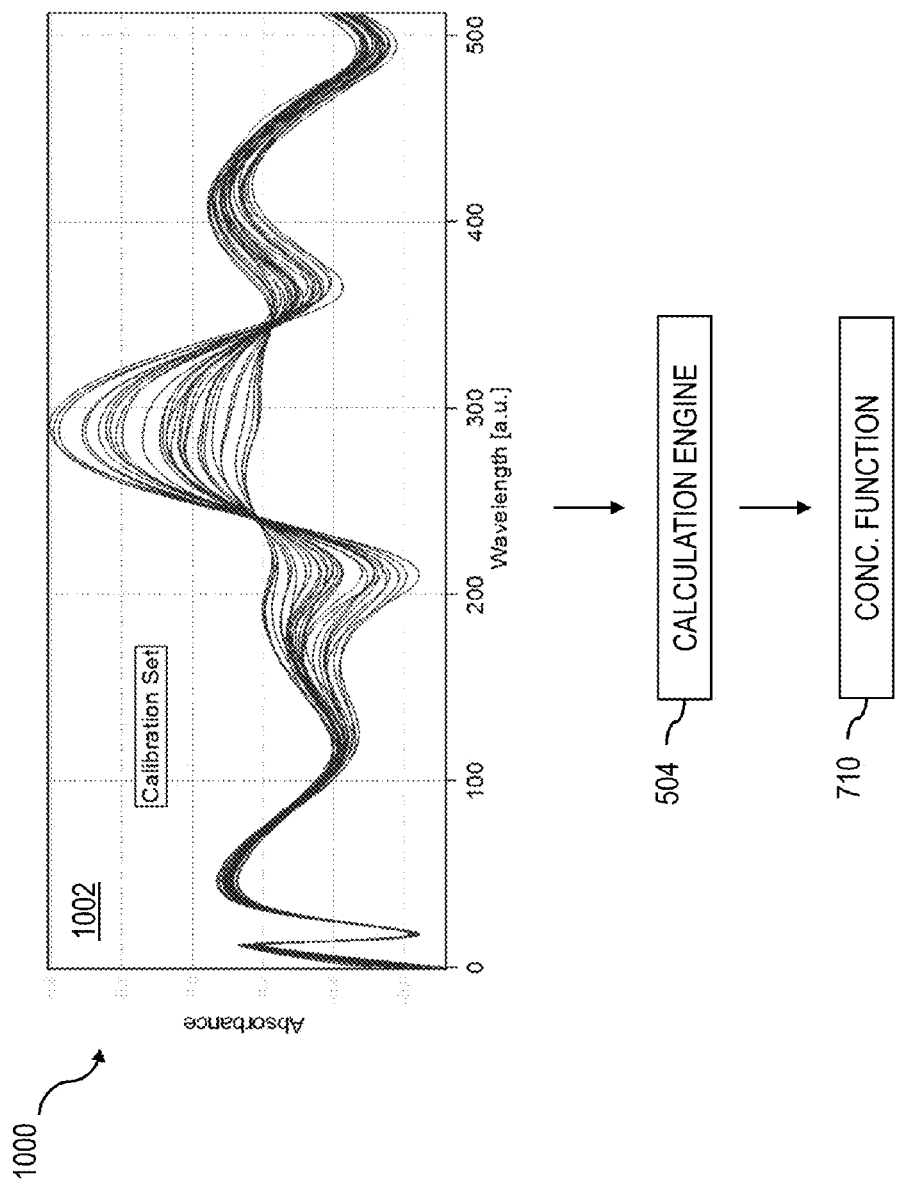
FIG. 10 shows a diagram illustrating features relating to generation of concentration model consistent with implementations of the current subject matter.

The method illustrated in the process flow chart 900 of FIG. 9 involves the use of one or more confidence indicators. A confidence indicator is a statistical tool to describe how well a calibration model can cover one or more field-measured samples. In implementations of the current subject matter, a confidence indicator can be used to determine the necessary measurement state change needed to best match the measurement state to a stored representation of an actual calibration state. Examples of confidence indicator functions that can be used in this manner include, but are not limited to, spectral residual, Mahalanobis distance, a variance indicators (e.g., mean squared error, root mean squared error, R-squared, or the like), etc. At design time, a concentration function (or concentration model) 710 is generated by a calculation engine 504 using as input a null calibration set 1002 as shown in the diagram 1000 of FIG. 10. The calibration function 710 can be loaded into memory or other computer-readable storage accessible by a spectroscopic analysis system controller 122 or other processor associated with a spectroscopic analysis system or otherwise receiving spectral data from a spectroscopic analysis system.

Figure 11:
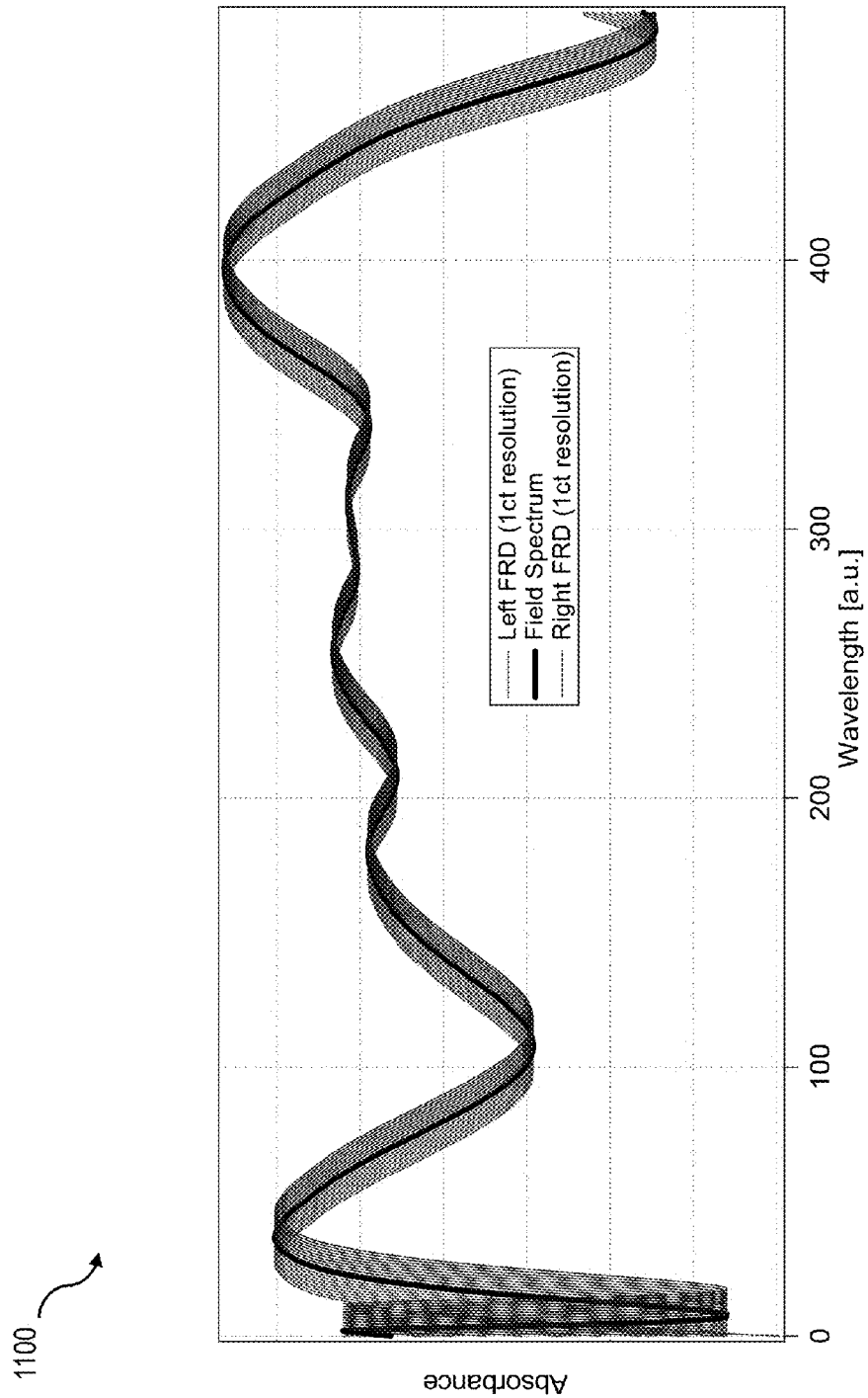
FIG. 11 shows a chart illustrating an example of mathematically altering a sample spectrum to create a predetermined number of variations consistent with implementations of the current subject matter.
Figure 12:
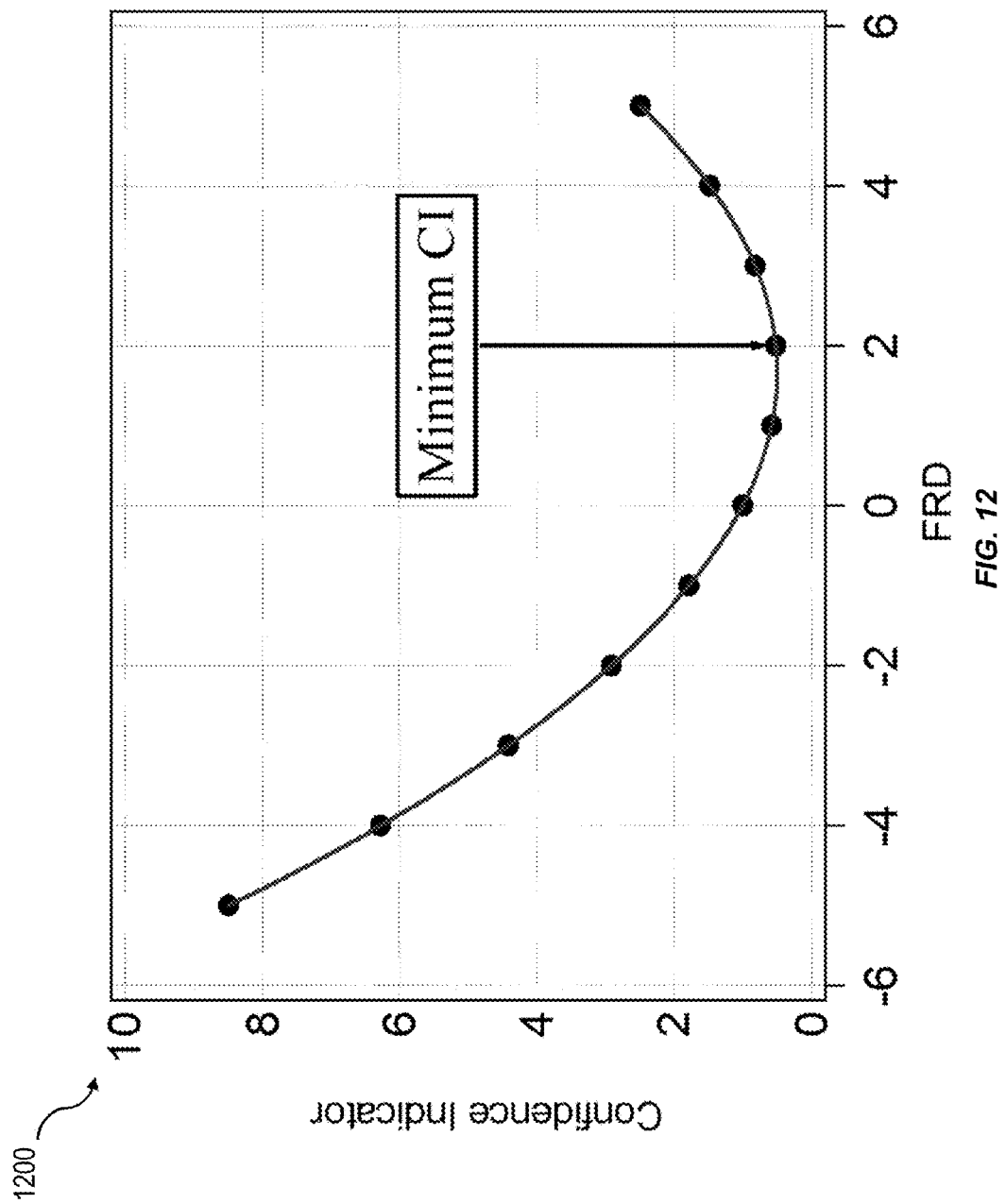
FIG. 12 shows a chart illustrating an example of determining an optimum confidence indicator consistent with implementations of the current subject matter.

As illustrated in FIG. 9, at 902, the method can include a computing device used for processing spectral data generated by a spectroscopic analysis system accessing a concentration model that includes one or more calibration functions 710. At 904, a frequency registration deviation of a field sample spectrum is mathematically altered to create a predetermined number of variations as shown in the chart 1100 of FIG. 11. These mathematical alterations can include linear or nonlinear frequency shifts, stretches, compressions, etc. of the field spectrum. The concentration model 710 is applied to all of the predetermined number of variations of the field spectrum before one or more confidence indicators are calculated for each of the variations of the field spectrum at 906. At 910, each confidence indicator or combination of more than one confidence indicator is modeled as a singlevariate function of the frequency registration deviation such that an optimum frequency registration deviation that either minimizes or maximizes the confidence indicator or the combination of confidence indicators is mathematically determined as shown in the chart 1200 of FIG. 12. At 912, the concentration function 710 is applied to the particular field spectrum variation that corresponds to an optimum frequency registration deviation to calculate an analyte concentration associated with that field spectrum, as the particular variation corresponding to the optimum frequency registration deviation is the variation that best matches the original calibration state of the spectroscopic analysis system.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to as programs, software, software applications, applications, components, or codes, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like. A computer remote from an analyzer can be linked to the analyzer over a wired or wireless network to enable data exchange between the analyzer and the remote computer (e.g. receiving data at the remote computer from the analyzer and transmitting information such as calibration data, operating parameters, software upgrades or updates, and the like) as well as remote control, diagnostics, etc. of the analyzer.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A computer-implemented method comprising:
quantifying a frequency registration deviation for a field spectrum collected during analysis by a spectroscopic analysis system of a sample fluid when the spectroscopic analysis system has deviated from a standard calibration state;
correcting the field spectrum based on the frequency registration deviation using at least one spectral shift technique; and
calculating a concentration for an analyte represented by the field spectrum using the corrected field spectrum.

2. A computer-implemented method as in claim 1, wherein the quantifying of the frequency registration deviation for the field spectrum comprises applying a set of calibration algorithms to the field spectrum.

3. A computer-implemented method as in claim 2, wherein the set of calibration algorithms comprises a concentration function for the spectroscopic analysis system; and wherein the quantifying comprises:
mathematically altering a frequency registration deviation of the field spectrum to create a predetermined number of variations;
calculating one or more confidence indicators for each variation of the field spectrum after applying the concentration function to all variations of the field spectrum; and
modeling each confidence indicator or a combination of more than one confidence indicator as a single-variate function of frequency registration deviation to mathematically determine an optimum frequency registration deviation that minimizes or maximizes the confidence indicator or combination of more than one confidence indicator.

4. A computer-implemented method as in claim 3, wherein the concentration function is based on an unmodified calibration spectral data set that does not include artificially generated frequency registration deviation spectra.

5. A computer-implemented method as claim 3, wherein the calculating of the concentration for the analyte comprises applying the concentration function to the field spectrum variation that corresponds to the optimum frequency registration deviation.

6. A computer-implemented method as in claim 2, wherein the set of calibration algorithms comprises an output of a calculation engine based on multivariate analysis of a set of calibration data representative of the standard calibration state of the spectroscopic analysis system.

7. A computer-implemented method as in claim 6, wherein the set of calibration data comprise artificially generated frequency registration deviation spectra generated at design time by applying mathematical shifts to calibration spectra collected using calibration samples.

8. A computer-implemented method as in claim 2, wherein the quantifying of the frequency registration deviation for the field spectrum comprises:
applying the set of calibration algorithms to calculate a characteristic indicator of frequency registration for the field spectrum; and
quantifying the frequency registration deviation for the field spectrum by comparing the characteristic indicator with a measured indicator of frequency registration determined from the field spectrum.

9. A computer-implemented method as in claim 8, wherein the measured indicator of frequency registration comprises one or more spectral features and/or a spacing between the one or more spectral features.

10. A computer-implemented method as in claim 1, wherein the quantifying of the frequency registration deviation for the field spectrum comprises using at least one frequency registration deviation function included in a set of calibration algorithms.

11. A computer-implemented method as in claim 1, wherein the correcting comprises:
correcting the field spectrum based on a quantified measurement state frequency registration deviation using the at least one spectral shift technique.

12. A computer-implemented method as in claim 11, wherein the at least one spectral shift technique comprises at least one of a linear shift, a nonlinear shift, a stretch of the measured spectrum, and a compression of the measured spectrum.

13. A computer-implemented method as in claim 11, further comprising applying the at least one spectral shift technique in one or more of a purely mathematical manner, via hardware tuning, and by using a combination of mathematical corrections and hardware tuning.

14. A computer-implemented method as in claim 1, wherein at least one spectral shift technique is applied to the entire field spectrum or to one or more individual sections of the field spectrum.

15. A computer-implemented method as in claim 1, wherein the spectroscopic analysis system comprises at least one of an absorption spectroscopic analysis system, an emission spectroscopic analysis system, a fluorescence spectroscopic analysis system, a Fourier transform infrared spectroscopic analysis system, a non-dispersive infrared (NDIR) spectroscopic analysis system, a cavity enhanced spectroscopic analysis system, a cavity ring-down spectroscopic analysis system, an integrated cavity output spectroscopic analysis system, a photoacoustic spectroscopic analysis system, and a Raman spectroscopic analysis system.

16. A computer-implemented method as in claim 1, wherein the spectroscopic analysis system comprises a sample cell to contain the sample fluid while a beam of light passes through the sample fluid at least once.

17. A computer-implemented method as in claim 1, wherein the spectroscopic analysis system comprises a free space volume in which the sample fluid is positioned while a beam of light passes through the sample fluid at least once.

18. A system comprising:
computer hardware comprising: at least one programmable processor; and
a machine-readable medium storing instructions that, when executed by the at least one programmable processor, cause the computer hardware to perform operations comprising:
quantifying a frequency registration deviation for a field spectrum collected during analysis by a spectroscopic analysis system of a sample fluid when the spectroscopic analysis system has deviated from a standard calibration state;
correcting the field spectrum based on the frequency registration deviation using at least one spectral shift technique; and
calculating a concentration for at least one analyte represented by the field spectrum using the corrected field spectrum.

19. A system as in claim 18, further comprising the spectroscopic analysis system, the spectroscopic analysis system comprising at least one of a laser light source and a non-laser light source disposed to cause a beam of light to pass through the sample fluid at least once, and a detector to quantify the field spectrum.

20. A system as in claim 19, wherein the spectroscopic analysis system comprises the laser light source, which comprises one or more of a semiconductor laser, a tunable diode laser, a quantum cascade laser, an intraband cascade laser, a horizontal cavity emitting laser, a vertical cavity surface emitting semiconductor laser, a distributed feedback laser, a distributed Bragg reflector laser, an external cavity tuned semiconductor laser, a gas discharge laser, a liquid laser, and a solid laser; or the spectroscopic analysis system comprises the non-laser light source, which comprises one or more of a light emitting diode, an incandescent source, a thermal source, a discharge source, a laser assisted source, a laser driven plasma source, a fluorescent source, a superluminescent source, an amplified spontaneous emission (ASE) source, a super-continuum source, a spectrally broad source, and a widely tunable QCL source with a tunable grating type waveguide filter.

21. A system as in claim 18, wherein the spectroscopic analysis system further comprises a sample cell to contain the sample fluid while the beam of light passes through the sample fluid at least once.

22. A system as in claim 18, wherein the spectroscopic analysis system further comprises a free space volume in which the sample fluid is positioned while a beam of light passes through the sample fluid at least once.

23. A computer program product comprising a machine-readable storage medium encoding instructions that, when executed by one or more programmable processors, cause the one or more programmable processors to perform operations comprising:

quantifying a frequency registration deviation for a field spectrum collected during analysis by a spectroscopic analysis system of a sample fluid when the spectroscopic analysis system has deviated from a standard calibration state;

correcting the field spectrum based on the frequency registration deviation using at least one spectral shift technique; and calculating a concentration for at least one analyte represented by the field spectrum using the corrected field spectrum.

\* \* \* \* \*